(12) United States Patent
Christensen (10) Patent No.: US 8,007,536 B2
(45) Date of Patent: Aug. 30, 2011

(54) DISC IMPLANT

(75) Inventor: Finn Bjarke Christensen, Silkeborg (DK)

(73) Assignee: FBC Device ApS, Aarhus C (DK)

( * ) Notice: Subject to any disclaimer, the term of this patent is extended or adjusted under 35 U.S.C. 154(b) by 546 days.

(21) Appl. No.: 12/086,145

(22) PCT Filed: Dec. 8, 2006

(86) PCT No.: PCT/DK2006/000699
§ 371 (c)(1),
(2), (4) Date: Jun. 6, 2008

(87) PCT Pub. No.: WO2007/065443
PCT Pub. Date: Jun. 14, 2007

(65) Prior Publication Data
US 2009/0270986 A1      Oct. 29, 2009

(30) Foreign Application Priority Data

Dec. 8, 2005   (DK) ................................. 2005 01746
Feb. 3, 2006   (DK) ................................. 2006 00153

(51) Int. Cl.
*A61F 2/44* (2006.01)
(52) U.S. Cl. .................................................. 623/17.14
(58) Field of Classification Search ..... 623/17.11–17.16
See application file for complete search history.

(56) References Cited

U.S. PATENT DOCUMENTS

| | | |
|---|---|---|
| 5,192,326 A | 3/1993 | Bao et al. |
| 5,258,031 A | 11/1993 | Salib et al. |
| 5,401,269 A | 3/1995 | Büttner-Janz et al. |
| 5,425,773 A | 6/1995 | Boyd et al. |
| 5,507,816 A | 4/1996 | Bullivant |
| 5,562,738 A | 10/1996 | Boyd et al. |
| 5,676,701 A | 10/1997 | Yuan et al. |
| 5,683,465 A | 11/1997 | Shinn et al. |
| 5,865,848 A | 2/1999 | Baker |

(Continued)

FOREIGN PATENT DOCUMENTS

EP         0 747 025        12/1996

(Continued)

OTHER PUBLICATIONS

Cunningham, "Basic scientific considerations in total disc arthroplasty", The Spine Journal, vol. 4 (2004), pp. 219S-230S.

(Continued)

*Primary Examiner* — Eduardo C Robert
*Assistant Examiner* — Summer Kostelnik
(74) *Attorney, Agent, or Firm* — McCarter & English, LLP (57) ABSTRACT

A problem with total disc implant surgery appears to be the positioning of the implant which if not correct may lead to pain and eventually new surgery. The present invention relates to an improved disc implant (1) for total disc replacement, comprising two inter-vertebral elements (2) which are flexibly connected via coupling means (4,5). Following surgery, the relative movability of said two inter-vertebral elements is decreased overtime, as bone ingrowth occurring around the implant and specifically through osseointegrative sections gradually degrease the movability of the elements relative to each other. Following, the relative movability of the implant elements is replaced by fixation of the elements. The fixation has flowingly occurred in a position affected by the movement of the patient, and is thereby more acceptable to the patient.

22 Claims, 10 Drawing Sheets

U.S. PATENT DOCUMENTS

| | | | |
|---|---|---|---|
| 5,899,941 A | 5/1999 | Nishijima et al. | |
| 5,928,284 A | 7/1999 | Mehdizadeh | |
| 5,976,187 A | 11/1999 | Richelsoph | |
| 6,019,792 A | 2/2000 | Cauthen | |
| 6,113,637 A | 9/2000 | Gill et al. | |
| 6,120,503 A | 9/2000 | Michelson | |
| 6,139,550 A | 10/2000 | Michelson | |
| RE37,005 E | 12/2000 | Michelson et al. | |
| 6,179,874 B1 | 1/2001 | Cauthen | |
| 6,280,475 B1 | 8/2001 | Bao et al. | |
| 6,371,988 B1 | 4/2002 | Pafford et al. | |
| 6,500,206 B1 | 12/2002 | Bryan | |
| 6,641,614 B1* | 11/2003 | Wagner et al. | 623/17.15 |
| 6,679,915 B1 | 1/2004 | Cauthen | |
| 6,733,533 B1 | 5/2004 | Lozier | |
| 6,783,721 B2 | 8/2004 | Higham et al. | |
| 6,846,328 B2 | 1/2005 | Cauthen | |
| 6,884,775 B1 | 4/2005 | Tabin et al. | |
| 6,913,621 B2 | 7/2005 | Boyd et al. | |
| 6,913,622 B2 | 7/2005 | Gjunter | |
| 6,972,037 B2 | 12/2005 | Zubok et al. | |
| 7,011,684 B2 | 3/2006 | Eckman | |
| 7,101,399 B2 | 9/2006 | Errico et al. | |
| 7,270,681 B2 | 9/2007 | Cauthen | |
| 2002/0077702 A1 | 6/2002 | Castro | |
| 2004/0030387 A1* | 2/2004 | Landry et al. | 623/16.11 |
| 2006/0173542 A1* | 8/2006 | Shikinami | 623/14.12 |
| 2006/0235529 A1* | 10/2006 | Ralph et al. | 623/17.14 |

FOREIGN PATENT DOCUMENTS

| | | |
|---|---|---|
| EP | 0 950 389 | 10/1999 |
| EP | 1 421 922 | 5/2004 |
| FR | 2 694 882 | 2/1994 |
| FR | 2 812 806 | 2/2002 |
| WO | WO 99/53871 | 10/1999 |
| WO | WO 01/62190 | 8/2001 |
| WO | WO 03/084449 | 10/2003 |
| WO | WO 2006/069463 | 7/2006 |
| WO | WO 2007/023399 | 3/2007 |

OTHER PUBLICATIONS

Itoh et al., "Development of a novel biomaterial, hydroxyapatite/collagen (Hap/Co1) composite for medical use", Bio-Medical Materials and Engineering, vol. 15 (2005), pp. 29-41.

Lehmann et al., "Biomechanical comparison of anterior cervical spine locked and unlocked plate-fixation systems", Eur Spine J, vol. 14 (2005), pp. 243-249.

Mayer, "Degenerative disorders of the lumbar spine Total disc replacement as an alternative to lumbar fusion", Orthopäde, vol. 34 (2005), pp. 1007-1020.

Saraph et al., "Evaluation of Spinal Fushion Using Autologous Anterior Strut Grafts and Posterior Instrumentation for Thoracic/Thoracolumbar Kyphosis", Spine, vol. 30 (14), pp. 1594-1601.

* cited by examiner

DISC IMPLANT

This application is a §371 national phase filing of PCT/DK2006/000699 filed Dec. 8, 2006, and claims priority to Danish Appln. No. PA2005 01746 filed Dec. 8, 2005; and to Danish Appln. No. PA20060153 filed Feb. 3, 2006.

All patent and non-patent references cited in the present application, are also hereby incorporated by reference in their entirety.

FIELD OF INVENTION

The present invention relates to the field of spine implants. The implant of the invention provides fusion with the body of the vertebra and stabilisation of the spine in an anatomic correct position. The invention relates to an improved disc implant for total disc replacement, comprising two inter-vertebral elements which are flexibly connected via coupling means. Following surgery, the relative movability of said two inter-vertebral elements is decreased overtime, as bone ingrowth occurring around the implant and specifically through osseointegrative sections will gradually degrease the movability of the elements relative to each other. Eventually fixation of the elements will occurred in a position affected by the movement of the patient, and thereby in a position more acceptable to the patient.

BACKGROUND OF INVENTION

Back pain is major problem in the adult population. The pain may have multiple causes, whereof some may require surgery. Lower back pain may be caused by displacement of the vertebrate bodies and the intermediate discs in the lumbar region of the spine and particular L4-L5 and L5-S1 are vulnerable. For patients with severe pain that doesn't respond to conservative treatment, fusion surgery may be an option. Spinal fusion surgery (fusing one vertebra to another) is often done to decrease motion at a painful motion segment to reduce associated pain at that segment. This abnormal and painful motion can be caused by painful discs (discogenic pain or degenerative disc disease), abnormal slippage and motion of the vertebra (spondylolisthesis or spondylolysis), or other degenerative spinal conditions, including but not limited to facet joint degeneration. In addition, a spine fusion may be indicated for any condition that causes excessive instability of the spine, such as certain fractures, infections, tumors, and spinal deformity (such as scoliosis).

Several treatment methods are known but further improvements are desired as the different methods all are associated with disadvantages.

During posterolateral spine fusion (PLF) surgery a graft is laid out in the posterolateral portion of the spine. Interbody surgeries may be performed either from the front or from the back and are thus described as Posterior lumbar interbody fusion (PLIF), Transforaminal lumbar interbody fusion (TLIF) and Anterior lumbar interbody fusion (ALIF). The different types of operation include removing the disc between two vertebrae and inserting bone into the space created between the two vertebral bodies. Posterior surgery leads to acceptable results and is claimed to further improve outcome by adding anterior column support as can be achieved by ALIF, TLIF or PLIF. The combined fusion procedures are generally defined as Circumferential fusion. These types of operations, where posterior stabilisation is needed, are unfortunately associated with a long recovery compared to exclusively anterior surgery.

In a further used technique the invertebra disc is replaced by an implant attached to the vertebra bodies above and below. Following surgery bone tissue grow around the implant and thereby fusion with the vertebra bodies is obtained.

The position of the vertebra bodies is decided during surgery by the fixation used or partly by the design of the implant used. Currently three types of Total Disc Replacement (TDR) implants have been used. Unconstrained designs appear to have some advantages as they are more likely to provide a physiologic mobile instantaneous axis of rotation (IAR), thus displaying a greater range of motion in vivo. Their lack of constraint may prevent excessive facet joint or capsuloligamentous loads in the extremes of flexion and extension. Furthermore, since the IAR is mobile, they may be less sensitive to small errors in implant placement. On the other hand, constrained devices appear to have an advantage in protection of the posterior elements from shear loading. Spinal shear loads of considerable magnitude occur during activities of daily living. A third group of implants are characterised as semi constrained implants including Prodisc, Maverick and Flexicore and are currently in use.

In general the position of the disc implants is determined during surgery as the fusion requires stabilization until bone growth has occurred which may often take several months (3-6 months). If the position is not correct the surgery may be inefficient or may even result in secondary effects caused by stress of the neighbouring discs. Subsequent surgeries are complicated by the previous surgery.

SUMMARY OF INVENTION

The present invention provides a disc implant for use in spine surgery and methods of spine surgery wherein said disc implant is used. The disc implants according to the invention enables fixation of the elements overtime, as an initial relative motion of the elements of the disc implant is lost over time by bone ingrowth and following fixation of the disc elements relative to each other.

The lack of success of operation may in several cases be attributed to fusion/fixation of implants in a suboptimal position. This may be due to the fact that the position of fusion/fixation is determined during surgery where the back is in a position different from the position employed during the awake hours when the patient is predominantly in a standing or seated position.

To account for this, the disc implant according to the invention allows relative motion of the elements of the disc implant. Meaning that in a period following surgery the elements of the disc implant will be movable in relation to each other, but also that the implant due to the stimulatory effect on bone growth will be fixed by bone ingrowth within a suitable period. This period of temporal movability allow the fixation to occur in a position affected by the life/motion of the patient, thus the position of fixation will be closer to the natural position of the patient and thus the likelihood of a successful recovery is increased.

An aspect of the invention relates to a disc implant for total disc replacement comprising;

a first inter-vertebral element having a first outer fusion surface and an internal coupling surface,     a second inter-vertebral element having a second outer fusion surface and an internal coupling surface,     coupling means for connecting said first and second inter vertebral elements, each element comprising osseointegrative sections enabling fixation of the first and second elements relative to each other overtime, wherein said first and second elements of the implant remain relatively movable for at least 1 day after insertion and the implant is converted into a fixed implant less than 12 month after insertion.

In one preferred embodiment the implant is 75% fixed after 1 month.

In order to enable and direct bone ingrowth it may be preferred that the osseointegrative sections of the first and second inter-vertebral element comprise openings or incisions. More preferred are embodiments of the invention where the openings of the first and second inter-vertebral element oppose each other when the elements are engaged with each other via the coupling means. Such an arrangement is optimal for fixation of the elements of the implant over time following insertion.

In order to have a disc implant of sufficient stability or tolerability the elements of the disc implant is preferably made of ceramic, polymers, and/or metals.

In one preferred embodiment the disc implant comprise openings filled with a suitable material, such as auto or allograft of bone, or a bioceramic material, which may allow and stimulate bone ingrowth. The bioceramic material may be selected from the group of: hydroxyapatite, tricalcium phosphate, or mixtures of the two.

In one embodiment the disc implant may comprise at least a partial coating, for protection of for stimulating bone fusion and/or bone ingrowth by inclusion of osteoinductive or osteogenic agents in the coating.

The disc implant according to the invention may be for anterior insertion, posterior, insertion or transforaminal lumbar interbody fusion An aspect of the present invention regards the ability of the disc implant to be supported by a posterior stabilisation means.

In a further aspect the invention relates to a method of treatment an individual in need thereof comprising;

insertion of a disc implant, wherein a first and second element of said disc implant remains relatively movable for at least 1 day after insertion and is converted into a fixed implant less than 18 month after insertion.

The inserted disc implant may comprise any of the features described for the disc implant according to the invention. The method of the invention relates to anterior, posterior insertion or transforaminal lumbar interbody fusion.

DETAILED DESCRIPTION OF THE INVENTION

The present invention relates to a disc implant for total disc replacement capable of stabilizing the spine. The disc implant stimulates fusion with the neighbouring vertebrate bodies and fixation over time of the disc implant in a physiologically acceptable position. The disc implant according to the invention may be used for insertion in the lumbar spine region.

Disc Implant

The disc implant according to the invention relates to a disc implant for total disc replacement. The implant generally comprises two elements, which are coupled together forming the disc implant. The top and bottom surface of the implant, when viewed as positioned in a standing individual, are referred to at as first and second outer fusion surfaces. The opposing surfaces of the two elements are described as internal coupling surfaces as means for coupling of the elements are conveniently located on this surface. The coupling means serve to connect the first and second inter vertebral elements. The coupling of the inter-vertebral elements regulates the movement of said first and second inter-vertebral element relative to each other. Thus coupling of said two inter vertebral elements does not firmly position the elements relative to each other. Minor movements of the elements in at least on direction should be possible when said elements are coupled.

Each first and second inter-vertebral element may be stabilised to the adjacent vertebral discs after insertion by suitable means until fusion with vertebral discs is obtained.

A fixed implant herein describes an implant wherein the elements of said implant are not movable relative to each other. Fusion of an implant, with neighbouring discs, occurs at the outer surface of the disc implant.

As described herein below the invention relates to the temporal nature of the movability of the first and second inter-vertebral elements relative to each other of the disc implant. Thus a first and second element of an implant according to the invention remains relatively movable for at least 1 day after insertion and is converted into a fixed implant less than 12 month after insertion.

An aspect of the invention relates to a disc implant comprising;

a first inter-vertebral element having a first outer fusion surface and a first internal coupling surface, a second inter-vertebral element having a second outer fusion surface and a second internal coupling surface, coupling means for connecting said first and second inter vertebral elements each element comprising osseointegrative sections enabling fixation of the first and second elements relative to each other overtime, wherein the first and second elements of the implant remains relatively movable for at least 1 day after insertion and the implant is converted into a fixed implant less than 18 month after insertion.

Shape

The disc implant according to the invention may have any shape that enables transient stabilization and stimulates long term fixation by fusion and bone ingrowth.

The shape of the disc implant, as seen from the top, may be such a round, circular, oval or oblate shape. In a preferred embodiment the disc has a concave portion providing a more anatomically acceptable shape to the disk. The implant may have a circumference with a kidney shape, wherein the concave portion is position to the back of the disc implant. The concave portion may be less than half of the outer circumference of the cross section of the disc implant, such as less than a ⅓ or such as less than a ¼ of the outer circumference of the cross section of the disc implant. Embodiments having a concave portion are shown in FIGS. 1-5.

Figure 5:
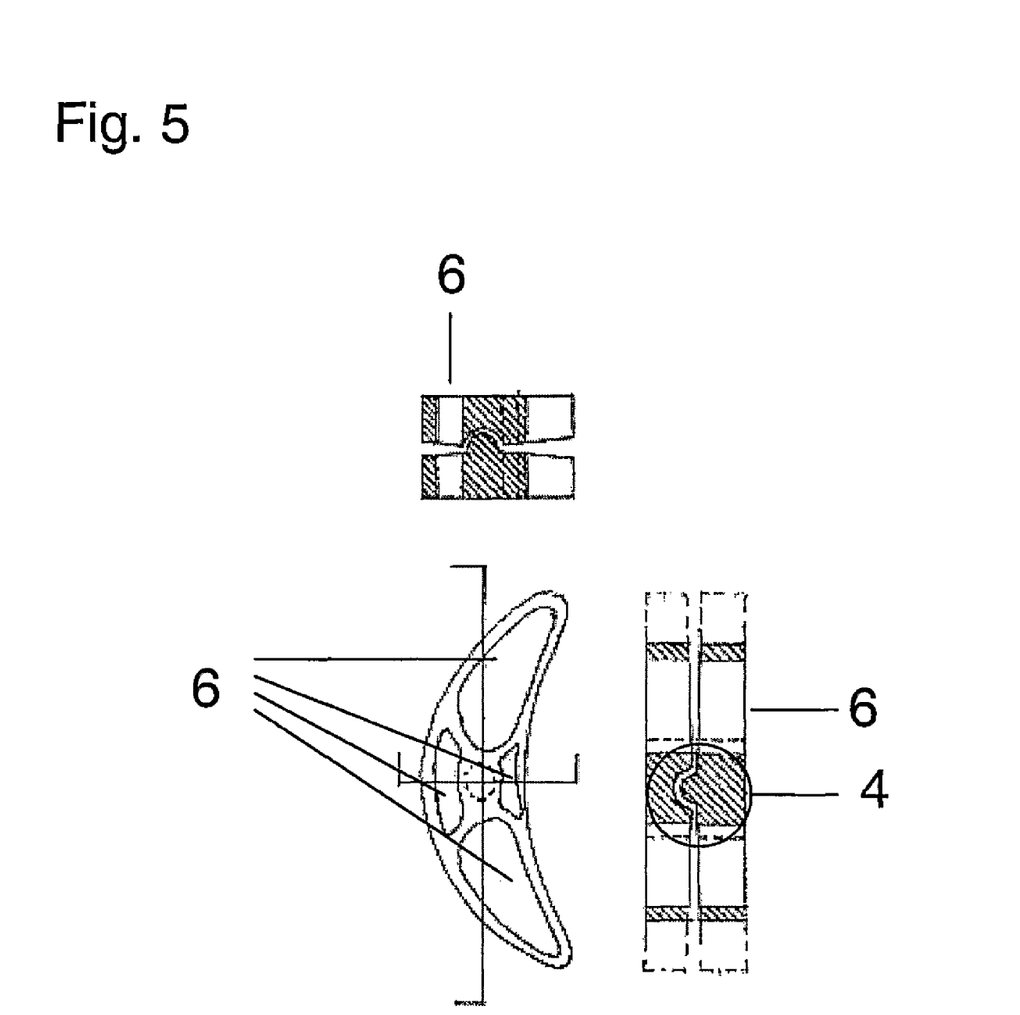
FIG. 5
Implants according to the invention for transforaminal lumbar interbody fusion.

The disc implant may be designed for posterior or anterior surgery, preferable anterior surgery, which may lead to a shorter recovering period after surgery. Alternatively, the implant may be designed for transforaminal lumbar interbody fusion (FIG. 5).

The implant may further be equipped with keels positioned on the first and second outer fusion surface prevention rotation of the implant (see FIG. 2).

Coupling Means

The coupling means of the first and second inter-vertebral elements should allow minor movements of the first and second inter-vertebral elements relative to each other. The coupling means are preferably located on the internal coupling surfaces of the first and second inter-vertebral elements.

The coupling means may be curved surfaces suited for engaging the two elements.

The first internal coupling surface may comprise a protuberance and the second internal coupling surface a concave indentation/depression suited for receiving said protuberance of the first internal coupling surface. Coupling means may thus be formed by a flange position at the first internal coupling surface and a slot for receiving such projection positioned at the second internal coupling surface. Alternative coupling means may be characterised as a "ball and socket arrangement". It is to be understood the position of the coupling means may be switched, thus said flange and said slot may be positioned on either of the elements. In further embodiment said couplings means may include a third element such as a ball or plate to be position in between said first and second inter-vertebral elements both having suitable slots for receiving such ball or plate.

The area/volume formed by the internal coupling surface of the inter-vertebral element may be referred to as the coupling zone of the implant.

In order to obtain temporal movability of the disc implant, coupling of said first and second inter-vertebral elements does not result in formation of a rigid disc implant. As illustrated in figures the coupling of the internal surfaces leaves some room for movement of the first at second element relative to each other in at least one direction.

Size

In one embodiment the circumference of the disc implant is smaller than the circumference of the corpus, particularly the basis of the corpus should protrude relative to the implant at the front of basis. It is preferred that the corpus protrude at least 0.2 mm, such as 0.4 mm, such as 0.6 mm past the edge of the implant. More preferably the distance from the edge of circumference of the implant to the edge of the corpus is at the most 5, such as 2 mm, such as at 1.5, such as 1.0 mm.

Such arrangement may provide stimulation of bone growth at the side of the disc implant and following fixation of the inter-vertebral elements (se below), when bone tissue join at the edge of the internal surfaces of the elements.

Material

The disc implant according to the invention may be of any material suitable for implantation. Thus the implant may be constructed from one or more materials selected from but not limited to the group of ceramic, polymers, and metals. Preferred are metals and ceramics. The material(s) may be in states of glassy, rubbery, semi-crystalline, or crystalline, before and/or after processing into the implant.

In one embodiment the implant is constructed of metal or metal alloys, selected from the group of but not limited to stainless steel, cobalt-chromium, titanium (Ti), titanium alloys, shape memory alloys, e.g. NiTi, Tantalum (Ta), niobium (Nb), zirconium (Zr) and platinum (Pt). Preferred metals and metal alloys are titanium, tantalum, titanium alloys, and cobalt-chromium and alloys thereof. Cobalt-chromium may be e.g. CoCrMo alloy. Titanium alloys may be e.g. Ti6Al4V. Stainless steel may be e.g. austenitic stainless steels, especially Types 316 and 316L and Ni-free stainless steel.

Metals such as transition metals may be used for the disc implant. Particular tantalum (Ta) which is corrosion-resistant is considered. Tantalum is very useful for implants because it is totally immune to the action of body liquids and is non-irritating. A second transition metal, titanium, which likewise is very corrosion resistant has a high stiffness and is physiologically inert is preferred. Titanium and tantalum has the unusual ability to osseointegrate. Furthermore the position of disc implants of these metals is easily analyzed by conventional photo diagnostic methods.

The ceramic may be selected from the group of but not limited to bioinert ceramics (alumina ($Al_2O_3$), partially stabilized zirconia ($ZrO_2$), silicon nitride ($Si_3N_4$)), bioactive ceramics (Hydroxyapatite ($Ca_{10}(PO_4)_6(OH)_2$) and bioglasses), and resorbable ceramics (Calcium phosphate ceramics, e.g., tri-calcium phosphate, $Ca_3(PO_4)_2$).

Apatite is a group of phosphate minerals, usually referring to: hydroxylapatite, fluorapatite, and chlorapatite, named for high concentrations of OH—, F—, or Cl—ions, respectively, in the crystal lattice. Hydroxylapatite is the major component of tooth enamel, and a large component of bone material. Hydroxylapatite is a naturally occurring form of calcium apatite with the formula $Ca_5(PO_4)3(OH)$, but is usually written $Ca_{10}(PO_4)_6(OH)_2$ to denote that the crystal unit cell comprises two molecules.

Hydroxylapaptite is easily accepted by the recipient, and provides substantial stimulation of bone in-growth.

Most of the calcium phosphate ceramics are crystalline substances. The crystals are subjected to heat treatment at high temperatures, and sintered to produce a bioceramic material. Chemically, they are hydroxyapatite, tricalcium phosphate, or mixtures of the two. They are supplied as powders, granules, porous or non-porous blocks.

Tricalcium phosphate is more porous than hydroxyapatite, and is biodegraded ten to twenty times faster. The sintering temperature also has an influence on the behavior of the finished product: Depending on manufacturing conditions, tricalcium phosphate will be totally resorbed within a few months, or take several years to be removed by bioresorption. In the body, it is partially converted to hydroxyapatite, which is biodegraded more slowly.

In one embodiment artificial bone material, such as resorbable ceramic granules, resorbable tricalcium phosphate (TCP) ceramic granules, is preferred. Other preferred ceramics are alumina and zirconia.

The implant may further be made of Glassy and pyrolytic carbon which is highly efficient for stimulating bone fusion.

The polymer may be selected from the group of but not limited to polylactides (PLA), polyglycolides (PGA), polyanhydrides, polyorthoesters, poly(D,L-lactic acid), poly(lactide-co-glycolide) (PLGA), poly-D,L-lactic acid-poly(ethylene glycol), polyphosphates, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), and poly(methacrylic acid), Preferred polymers are PLA, PGA, and PLGA.

The implant may be made of one or more suitable materials. In one embodiment the implant is made of at least one of the materials mentioned above. In further embodiments the implant is made of at least two different materials. Either material may constitute such as between 1 and 90 percent of the total volume of the entire implant. One material may constitute 1-10% such as 10-20%, e.g. 20-30%, such as 30-40%, e.g. 40-50%, such as 50-60%, e.g. 60-70%, such as 70-80%, e.g. 80-90% of the total volume of the entire implant. The elements of the implant may comprise a central core of a metal surrounded by a layer of resorbable ceramic material.

The resilience of the material of the disc implant is preferably of an order similar to the resilience of bone.

One or more elements or part of elements may be covered by a coating layer of a particular material in order to optimize function.

Coating

Coating of the implant can be performed to protect the implant from body fluids including blood at the time of implanting as well as in a period followed implanting. A coating may alternatively or in addition be used for controlling bone growth in the vicinity of the implant by including suitable compounds.

In one embodiment the implant as described herein may be coated on the outer fusion surface, the internal coupling surfaces or the internal surface of the openings of the elements or any part of each surface or any combination of surfaces. In a preferred embodiment the internal surface of the openings is coated.

The coating comprises at least one layer of a coating material. The coating material may be selected from any suitable material. The said coating may include osteoinductive and/or osteogenic agent(s) as described here below. The coating may further comprise antibiotics.

By 'coated' is meant that the said coating material may be situated only on the outside of the coated surface. The thickness of the said coating may be such as less than 1 mm, 0.5 mm, such as 0.25.

The thickness of said coating may also at different surface points of the implant. The coating of one or more of the disc implants according to the invention may be performed by dipping the elements into a solution of or with the coating material for a predetermined time. The said coating material may also be sprayed onto the implant; another possibility is to apply the said coating by brushing.

Coating Material

In one embodiment the protective coating comprises material selected from the group of polylactides (PLA), polyglycolides (PGA), polyanhydrides, polyorthoesters, poly(D,L-lactic acid), poly(lacide-co-glycolide) (PLGA), poly-D,L-lactic acid-polyyethylene glycol, polyphosphates, poly(lactide-co-glycolide) composited with gelatine sponge, poly(2-hydroxy ethyl methacrylate), poly(N-vinyl pyrrolidone), ethylene vinyl acetate (EVA), poly(methyl methacrylate), poly(vinyl alcohol), poly(acrylic acid), polyacrylamide, poly(ethylene-co-vinyl acetate), poly(ethylene glycol), poly(methacrylic acid), Homopolymers of L-PLA and poly-caprolactone (PCL), Poly(orthoesters), like poly(anhydrides) and Pseudo-poly(amino acids).

In a second embodiment, said coating contains biologically active components, e.g. osteoinductive and/or osteogenic agent(s) or antibiotics. As examples, the inclusion of osteoinductive and/or osteogenic agents in said coating may induce early osteogenic processes, e.g. chemotaxis of specific cell classes, while the inclusion of antibiotics may reduce or prevent microbial infection.

Osteoinductive and/or osteogenic agents which also can be denoted as 'growth factors' are proteins that bind to receptors on the cell surface, with the primary result of activating cell migration, cellular proliferation and/or differentiation. Many osteoinductive and/or osteogenic agents are quite versatile, stimulating cellular division in numerous different cell types, while others are specific to a particular cell-type.

Materials that are considered osteo-inductive contain morphogens, such as Bone Morphogenetic Proteins. Morphogens initiate tissue and organ system development by stimulating undifferentiated cells to convert phenotypically.

Suitable growth factors which may be used include, but are not limited to, tissue growth enhancing substances such as growth and differentiation factors include platelet-derived growth factor (PDGF), transforming growth factor (TGF), acidic and basic fibroblast growth factor (FGF), insulin-like growth factor (IGF), bone morphogenetic proteins (BMPs) and combinations thereof.

In one embodiment the osteoinductive and/or osteogenic agent is selected from the group of Bone Growth Factors: platelet-derived growth factor (PDGF) (PDGF-AA, -AB, -BB), insulin-like growth factors I and II (IGF-I, IGF-II), fibroblast growth factors (FGFs) (acidic FGF—aFGF, basic FGF—bFGF), transforming growth factor beta (TGF-B) (TGF-B (TGF-Bs 1, 2, 3, 4, and 5)), osteoinduction and bone morphogenetic protein (BMP) (BMP-1, BMP-2, BMP-3, BMP-4, BMP-5, BMP-6, BMP-7, BMP-8, BMP-9, BMP-10, BMP-11, BMP-12), Epidermal Growth Factor (EGF), Cementum-Derived Growth Factor (CGF), Parathyroid Hormone-Related Protein (PTHrP). Preferred growth factors or osteoinductive and/or osteogenic agents are the Bone Morphogenetic Proteins (BMP-1, BMP-2, BMP-3, BMP-4, BMP-5, BMP-6, BMP-7, BMP-8, BMP-9, BMP-10, BMP-11, BMP-12) and Platelet-derived Growth Factors (PDGF) (PDGF-AA, -AB, -BB).

A coating may comprises at least one osteoinductive and/or osteogenic agent, such as 2 agents, e.g. 3 agents, such as 4 agents, e.g. 5 agents, such as 6 agents, e.g. 7 agents, such as 8 agents, e.g. 9 agents, such as 10 agents. Preferred is when a coating comprises 1, 2 or 3 osteoinductive and/or osteogenic agents. More preferred are 1 or 2 osteoinductive and/or osteogenic agents.

One or more layers of the said coating mater may be placed on the implant. In case of two or more layers, these layers may be equal or different in composition and one or more layers may contain osteoinductive and/or osteogenic agent(s) or other biologically active components.

Alternatively these osteoinductive and/or osteogenic agents may be comprised by one or more of the materials forming the elements of disc implant, thus the implant may be design for secretion of one or more of said osteoinductive and/or osteogenic agents, whereby stimulation of bone growth is directed by the elements of the disc implant. The disc implant preferably encourages bone formation while inhibiting osteoclast activity and bone resorption.

Osseointegrative Section

The first and second inter-vertebral elements of the invention may according to the invention comprise osseointegrative sections. Such sections having the capacity of stimulating and directing bone growth. The inter-vertebral elements may stimulate bone growth for fusion of each element to the neighbouring vertebral elements. The inter-vertebral elements according to the invention, further direct bone ingrowth for fixation over time of the elements relative to each other. Hereby the temporal movability of the first and second elements of the disc implant is displaced by fixation of the first and second inter-vertebral elements within a period of time after insertion. Thus the inclusion of osseointegrative sections enables fixation of the first and second elements relative to each other over time.

A fixed implant herein describes an implant wherein the elements of said implant are not movable relative to each other, while fusion of an implant, with neighbouring discs, occurs at the outer surface of the disc implant.

The inner and outer surface of the first and second inter-vertebral elements may comprise osseointegrative sections designed for optimisation of bone ingrowth according to the invention. As described here below, the osseointegrative sections may be openings, such as holes and incisions in the surface of the elements, which provide entry points for bone ingrowth. The osseointegrative sections may comprise suitable osteoinductive and/or osteogenic agents, and/or osteoinductive and/or osteogenic materials, and are as such referred to as filled.

In a preferred embodiment the disc implant for total disc replacement according to the invention comprises;
  a first inter-vertebral element having a first outer fusion surface and an internal coupling surface,
  a second inter-vertebral element having a second outer fusion surface and an internal coupling surface,
  coupling means for connecting said first and second inter vertebral elements,
  each element comprising osseointegrative sections enabling fixation of the first and second elements relative to each other overtime,
  wherein said first and second elements of the implant remain relatively movable for at least 1 day after insertion and the implant is converted into a fixed implant less than 18 month after insertion.

Openings

In one embodiment the inter-vertebral elements comprise one or more openings suitable for bone ingrowth, such openings being sufficiently large to allow entrance and sustain the viability of osteoblasts and osteogenic cells. The openings proceed through the inter-vertebral elements of the invention and allows ingrowth of bone through the elements. The openings may have any shape or size compatible with the elements of the disk implant. The figures herein show embodiments comprising a plurality of holes of different sizes and shapes (FIGS. 1-5).

Figure 2A:
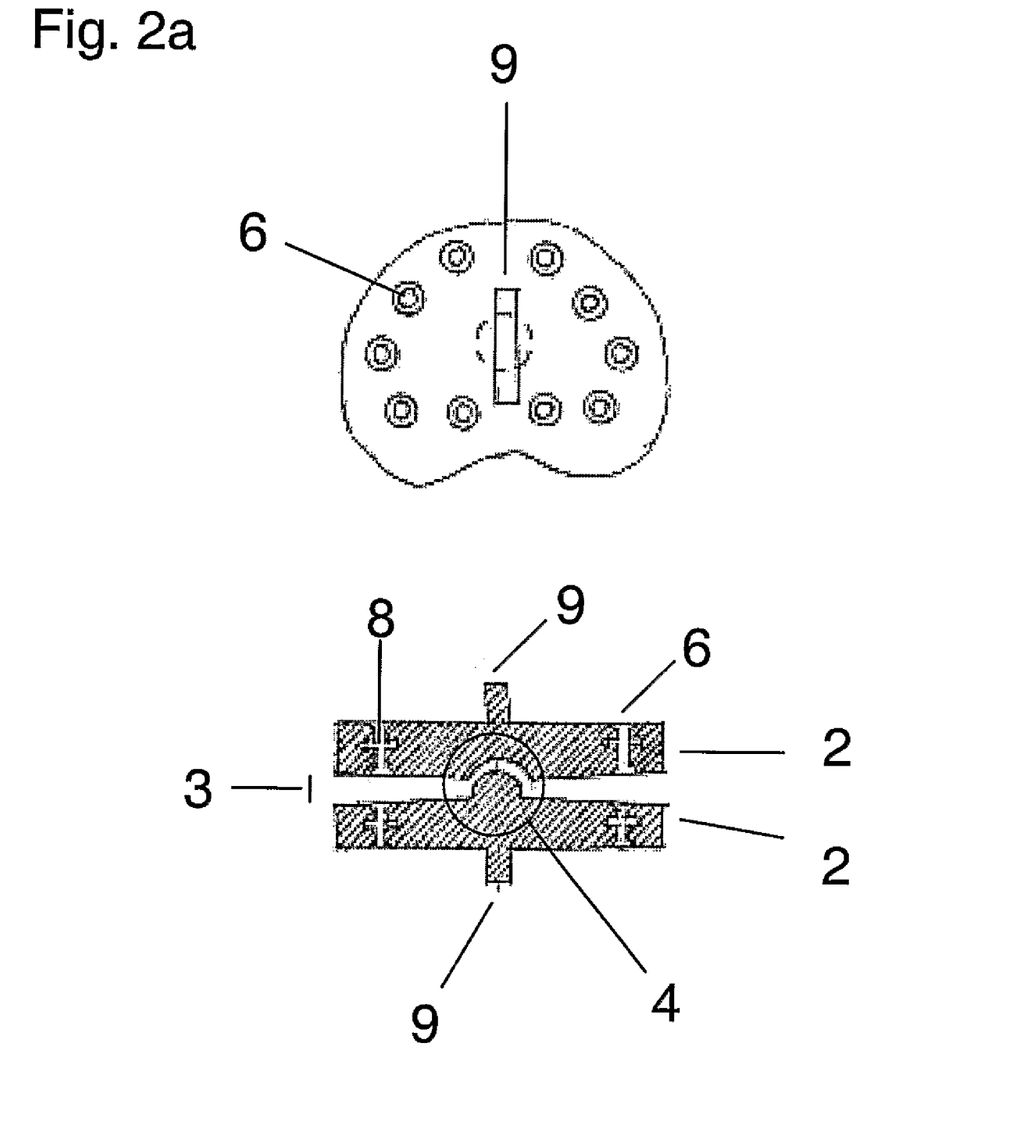
FIG. 2
Implants according to the invention with openings formed by channels with changing diameter and a void volume.
Figure 2B:
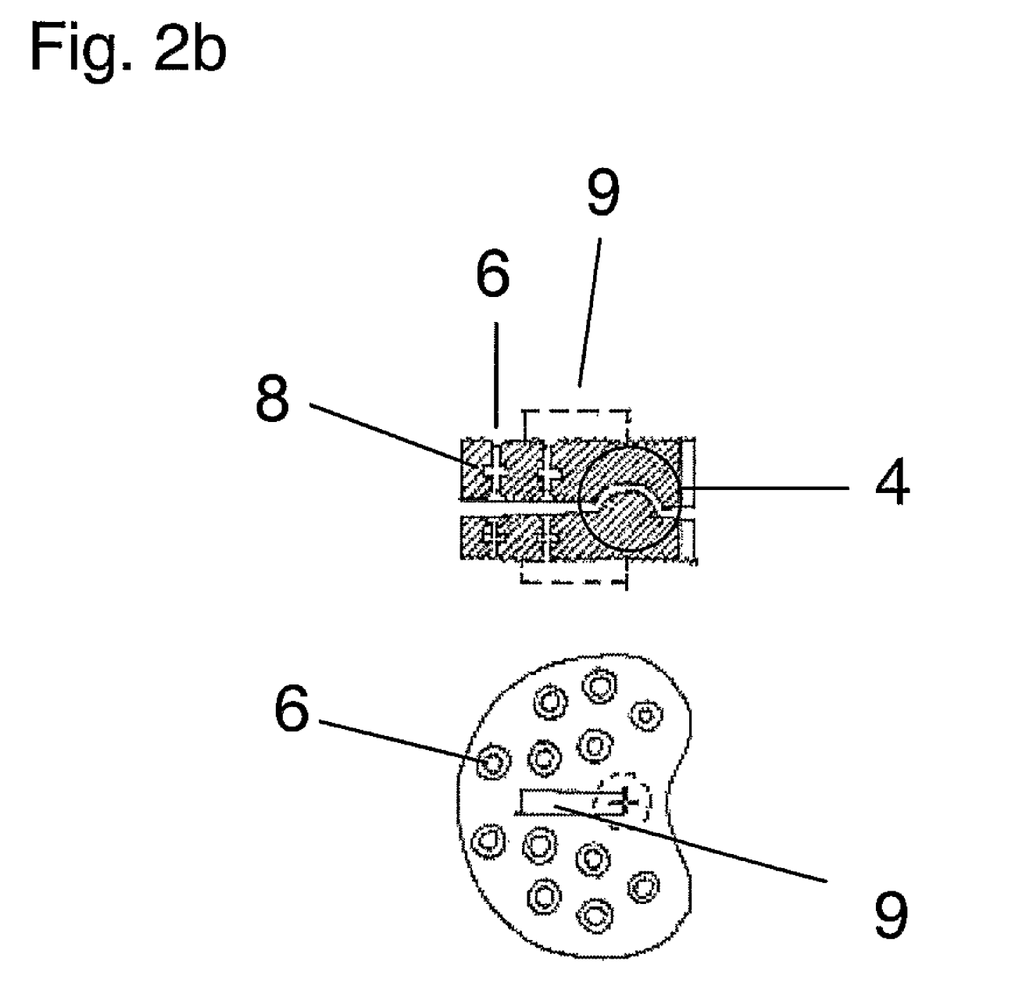

The openings may constitute straight channels through the element. In some embodiments the diameter of the opening vary through the element as seen in FIGS. 2a and 2b, displaying examples wherein the diameter of the opening channels are expanded with an internal void in the element.

The area of the fusion surface or the internal coupling surface occupied by the openings should be at least 5%, such as 10%, such as at least 15% in order to stimulate sufficient ingrowth of bone. In preferred embodiments, the area covered by the openings/holes is preferably 10-40%, 20-35%.

The openings and the internal void volume may constitute 10-90% of the bulk volume of the disk implant elements, such as 20-80%, preferably 30-70%, more preferred 40-60%, most preferably 30-60% of the bulk volume of the elements.

When referring the bulk volume of the elements the volume of the coupling zone is not included, but merely the approximate volume of the individual elements including the volume of said openings and internal void volume if present.

In a preferred embodiment the one or more openings of the first and second inter-vertebral elements are opposing each other when the elements are engaged with each other via the coupling means. Such an arrangement is illustrated in FIGS. 1, 2, 3 and 4. This arrangement provide optimal conditions for promoting bone ingrowth though both inter-vertebral elements e.g. fusion of the disk implant at each outer surface and following fixation (se below) of the disc implant elements relative to each other when bone tissue is formed in the coupling zone formed by the internal surface of the inter-vertebral elements.

Minor openings on the surface of the element may be denoted pores, which affect the capabilities of the implant to stimulate bone growth at the surfaces. The level of porosity, pore size distribution, pore morphology, and the degree of pore interconnectivity of implants significantly influences the extent of bone growth. The optimum pore volume to encourage osteoinduction is 150-500.

Figure 3A:
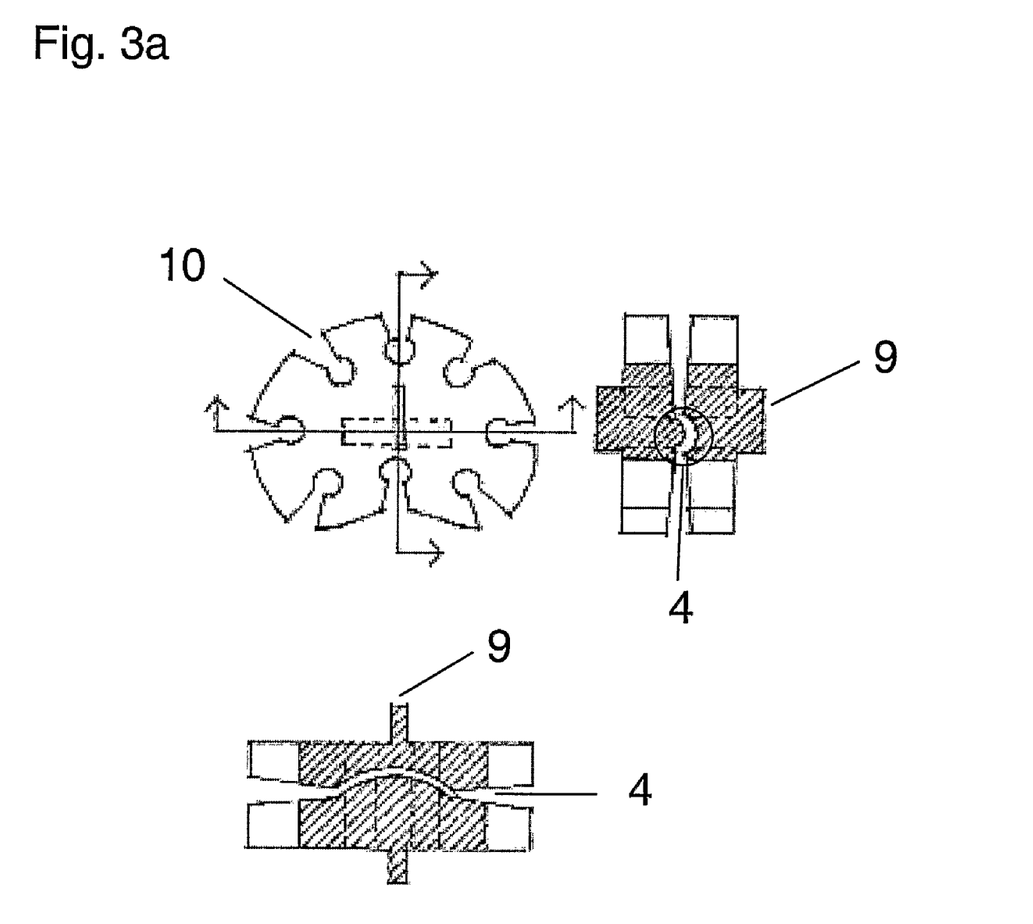
FIG. 3
Implants according to the invention with incision or openings and incisions FIG. 4
Implants according to the invention with large openings or filled openings.
Figure 3B:
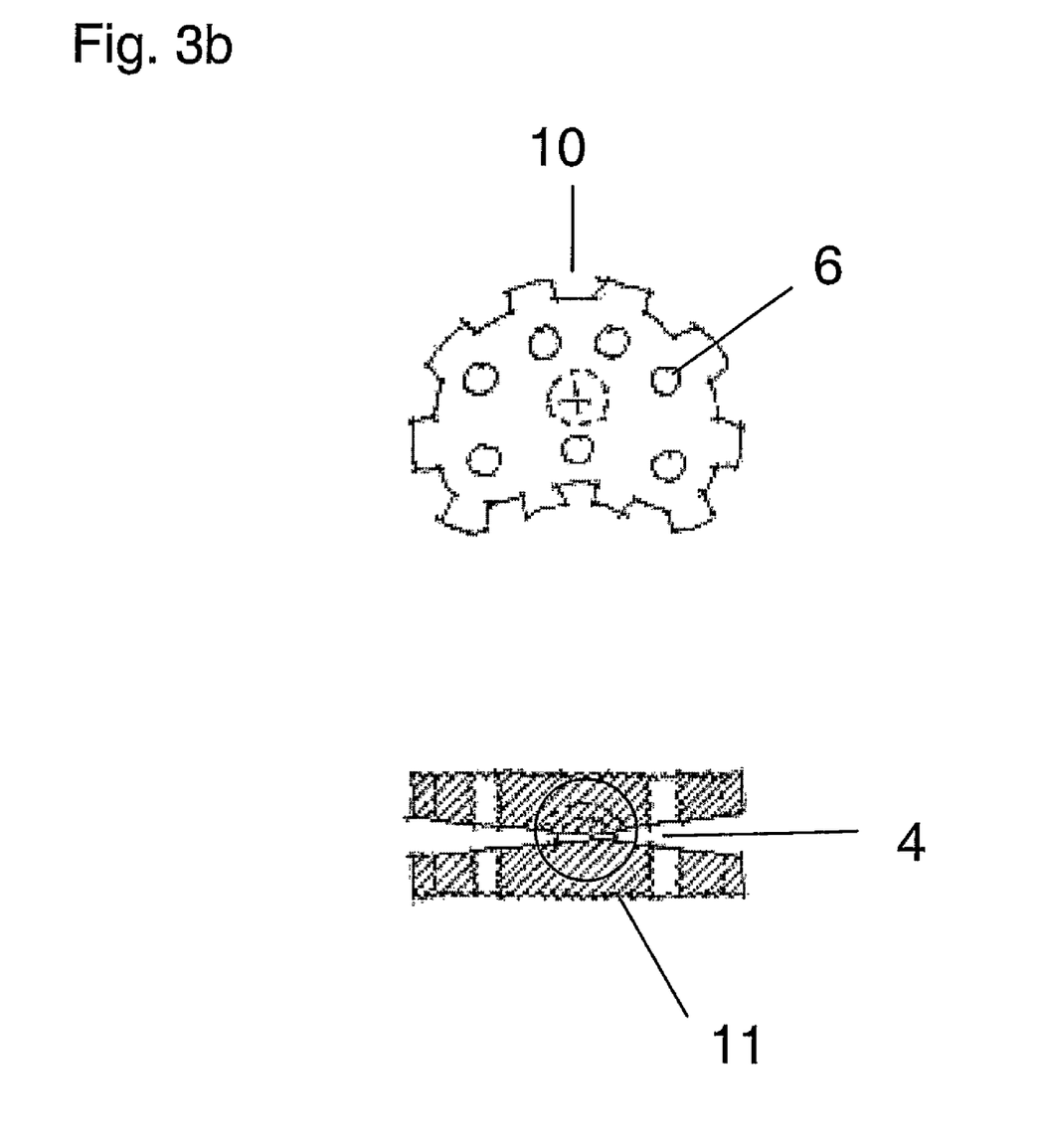

The surfaces of each element may further be rough, rugged or granular as depicted in FIG. 3b.

Incisions

Alternative or in combination with openings the elements may have incisions of any shape of the outer circumference (FIG. 3a). Incisions and openings may further be combined (FIG. 3b).

These openings and incision may stimulate osteoconduction, by providing a scaffold for the cells to move into and create new bone.

As seen above the elements of the disc implant may be made of one or more different material. In one embodiment a filling may be located in the openings/incision of the disc implant whereby a filled implant is obtained; such filling may comprise material suitable for directing and/or stimulating ostegenic activity and or inhibition of bone resorbtion. Auto or allograft of bone can be used. Artificial bone materials as ceramic materials are preferred. Resorbable materials, such as resorbable ceramic granules are more preferred, allowing bone formation in the openings within a suitable time. The implant may according to the invention be filled with resorbable materials, such as resorbable ceramic granules, which by suitable packaging may aid timing and extent of bone ingrowth.

In further embodiment the filling may comprise osteoinductive and/or osteogenic agent(s) as described in relation to coatings.

Temporal Movability

The disc implant according to the invention may fuse with the surrounding vertebrae, particularly the outer fusion surface of the inter-vertebral elements are suited for fusion with the neighbouring bones.

The characteristics and arrangement of the first and second inter-vertebral elements according to the invention provides a temporal movability of the elements relative to each other. The elements of the disc implant according to the invention are constructed to stimulate osteoconduction—i.e. the channeling of bone growth through the implant. This bone ingrowth leads to fixation of the first and second element relatively to each other, over time and thereby displaces the temporal movability of the first and second element of the disc implant.

The temporal movability of the first and second element is displaced by fixation of the disc implant in a physiologically acceptable position, as the implant during the days to weeks following insertion will adapt to a position affected by the posture of the recipient and thus fixation by bone ingrowth of the implant will occur at this position and not in a position determined during the surgical procedure inserting the implant.

In an embodiment the fixation of the first and second element, relative to each other leading to the formation of a fixed implant, is caused by bone ingrowth, said ingrowth occur preferably predominantly through the osseointegrative section of the elements of the disc implant.

In an embodiment the elements of the first and second element of the disc implant remain relatively movable for more than 8 hours, such as more than 16 hours, and preferably more than 24 hours. It is more preferred that the elements of the disc implant remain relatively movable for at least 1 day, such as 2 days or such as at least 3 days or more preferred more than 4 or 5 days. In particular embodiments the disc implant elements retain movability for 1- 90 days, 3-30 days, such as 25 days or 20 days after insertion.

In an embodiment the disc implant is converted to a fixed implant, wherein the relative movability of the first and second element of the disc implant are fixed relative to each other less than 18 or preferably less than 12 more preferably less than 8 or more preferably less than 6 months after insertion. Preferably the elements are fixed relative to each other within 3-12 months, such as more preferably within 5-10 months most preferably within 6-9 months after insertion.

The elements of the disc implant according to the invention are temporally moderately movable relative to each other in at least one direction.

As the fixation of the disc implant is a gradual process the degree of fixation or movability may be evaluated after implantation. It is further considered that the process of fixation will occur with different kinetics in different subjects.

The disc implant according to the invention is at least 65%, 70%, preferably 75%, more preferably 80% or such as 85% fixed after one week. In a preferred embodiment the disc implant is at least 90%, such as 92%, 95% fixed after 1 month.

It is an object of the present invention, that the device can be combined with a posterior stabilisation means. The posterior stabilisation can be in form of flexible (dynamic), semi-rigid or rigid implants, such as pedicle screws or facet joint screws or any other fixation/stabilisation method known in the art.

Method of Treatment

Individual suffering from lower back pain resulting from spine injury of other disease may obtain relief by an insertion of a disc implant. Back pain may be associated with disease such as Degenerated disk diseases and Central herniated disc.

An aspect of the present invention relates to a method of treatment an individual in need thereof comprising:
  insertion of a disc implant
    wherein a first and a second element of said disc implant remains relatively movable for at least 1 day after insertion and said implant is converted into a fixed implant less than 18 month after insertion.

In an embodiment the method includes insertion of a disc implant as described herein.

In further embodiments the method is for anterior, posterior and or transforaminal insertion.

The method of the invention for insertion of a disc implant may further be combined with posterior stabilisation means.

DETAILED DESCRIPTION OF THE DRAWINGS

Wording Used in Figures

1. Disc implant
2. Disk element
3. Coupling zone
4. Coupling means
5. Protrusion/slot arrangement
6. Openings
7. Convex relation ship
8. Internal void volume
9. Keels
10. Incisions
11. Outer surface
12. Filled openings

FIG. 1.

Figure 1A:
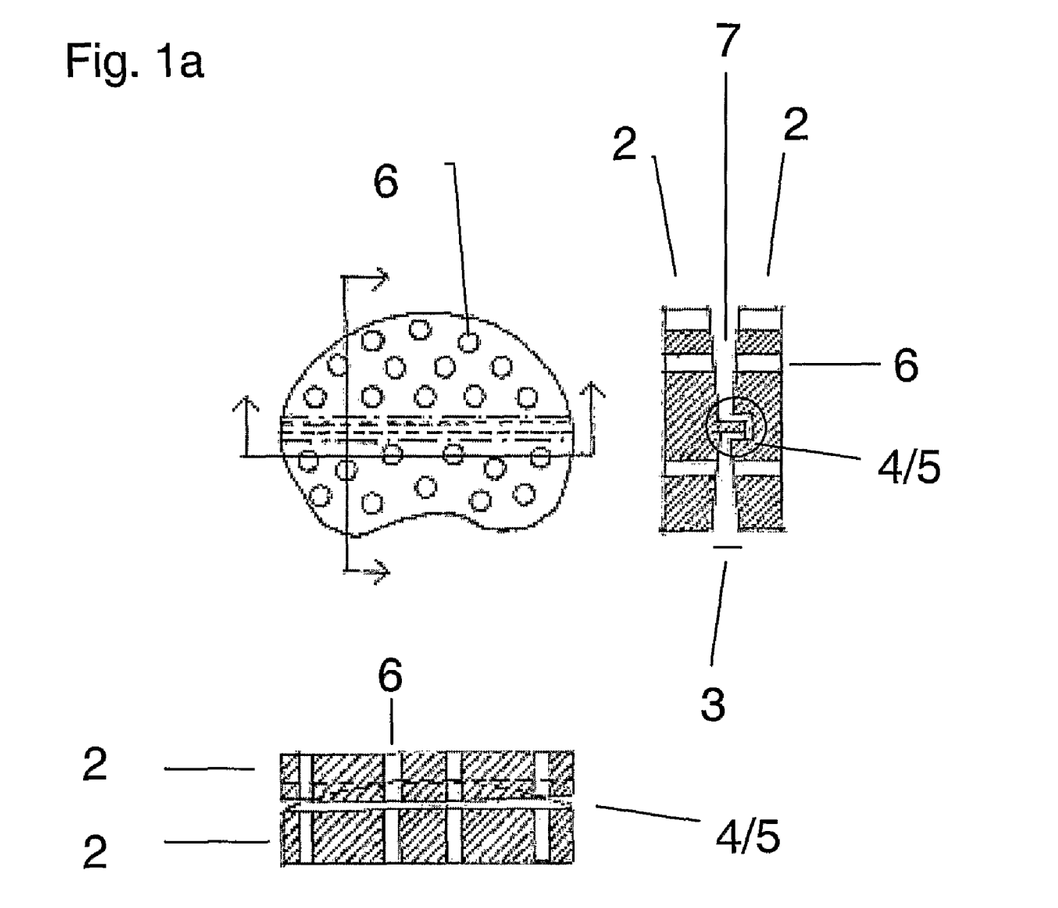
FIG. 1
Implants according to the invention with openings formed by straight channels.
Figure 1B:
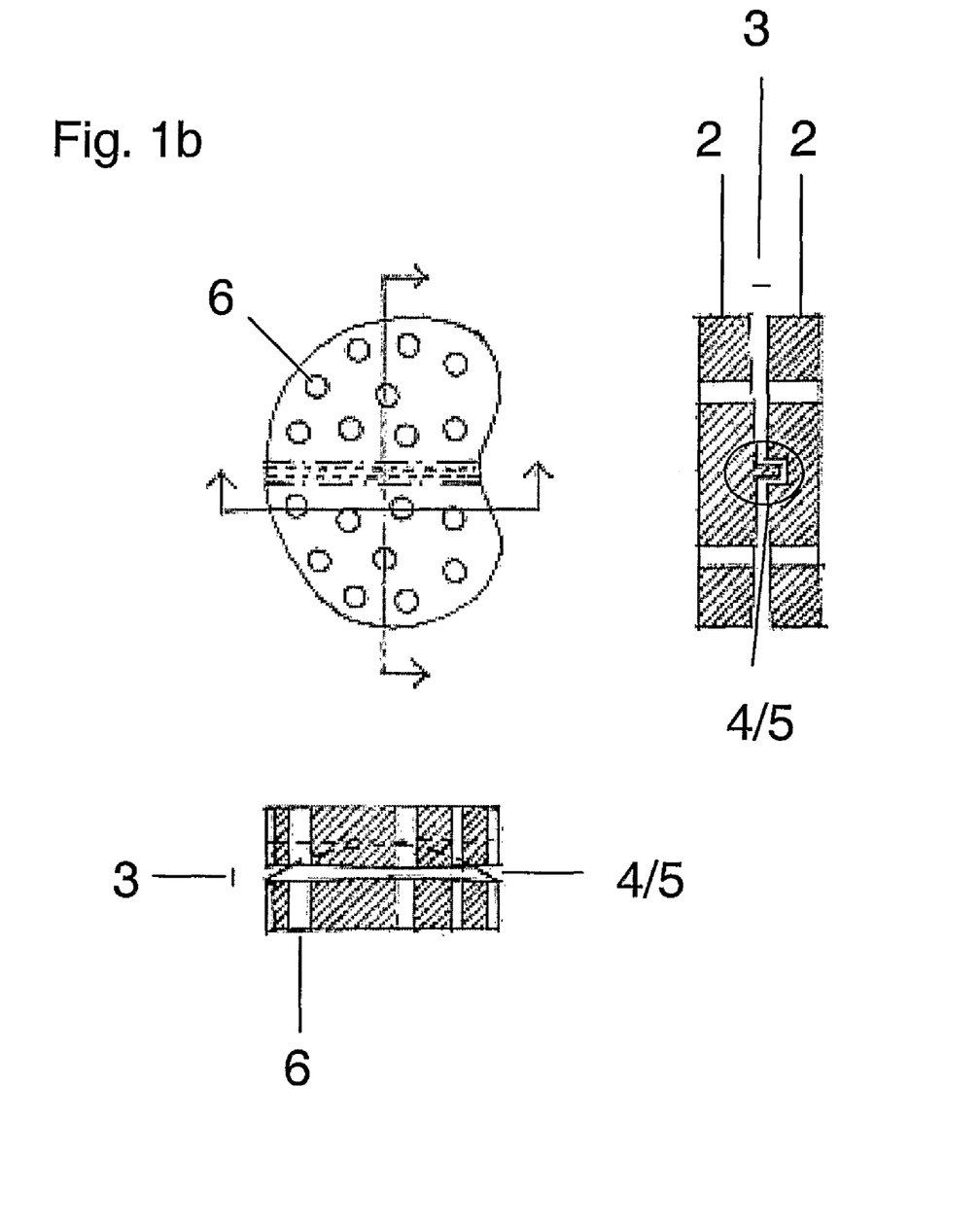
Figure 1C:
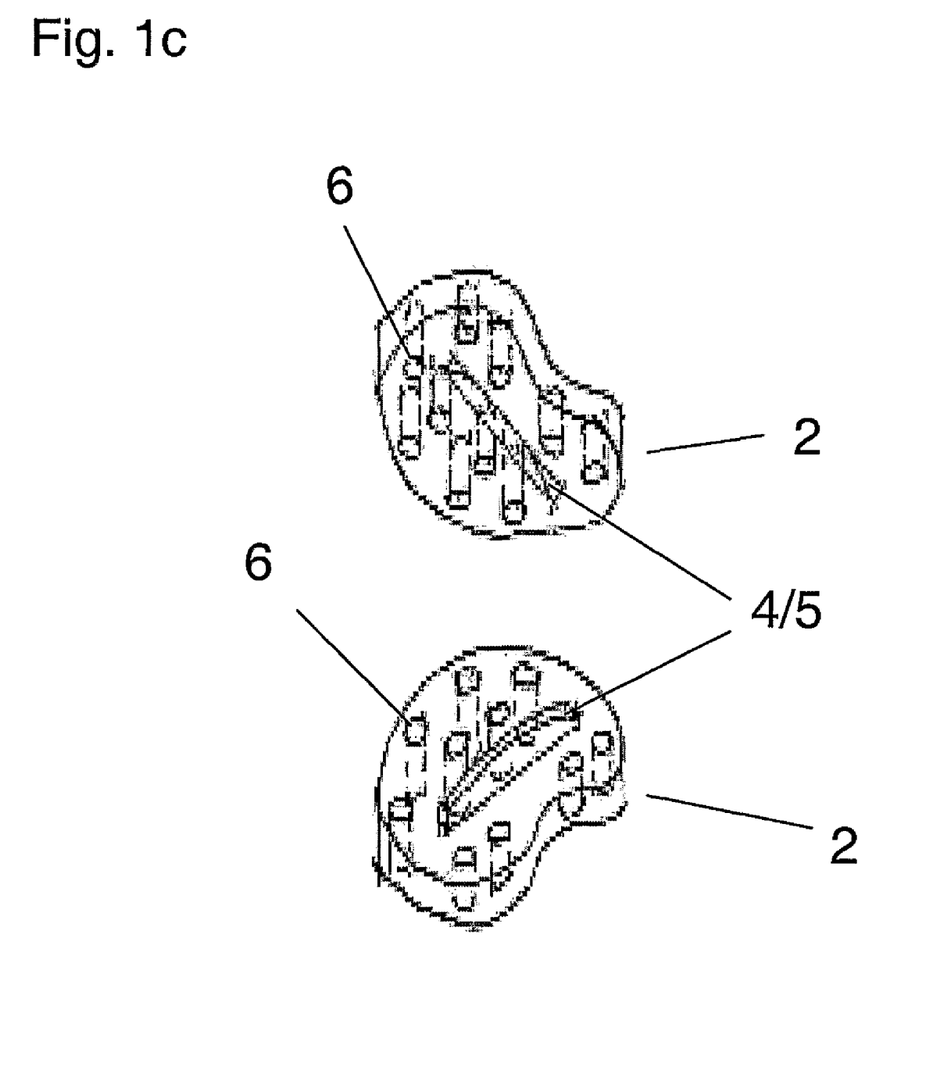

The figure shows examples of a kidney shaped disc implants according to the invention. FIG. 1a. Graphic illustration of the disc implant (1) viewed from above, and cross sections orthogonal to each other showing the openings e.g. straight channels (6) of this embodiment. The convex relation ship (7) of the two elements (2) is illustrated as well as the coupling means (4) of the disc implant provided by a curved protrusion engaged in a slot of the opposing element (5). The figure further illustrates the opposing position of the opening channels of the elements. FIG. 1b is an embodiment of the invention depicted as the embodiment of FIG. 1a, wherein the coupling means (4) are arranged across the shortest "diameter" of the elements. FIG. 1c shows an implant with few openings (6) than the implant of FIG. 1a, wherein the coupling means (4) are formed by a protrusion/slot arrangement (5) which does not extend across the entire length of the elements.

FIG. 2

Further examples of disc implants according to the invention comprising openings with an internal void volume are shown. The diameter of the channel through the elements varies and a void volume (8) is seen in both 2a and 2b. The embodiment depicted in 2a is differentiated from the embodiment shown in FIG. 2b by the number and position of the openings (6). A further difference is seen by the localisation of the coupling means (4). The figures further shows keels (9) positioned on the first and second outer fusion surfaces prevention rotation of the implant.

FIG. 3

Two embodiments according to the invention are shown comprising incisions (10) (3a) and opening (6) and incisions (10) (3b). Different coupling means (4) are further illustrated by a long and narrow projection in 3a and a small circular protuberance in 3b engaged in suitable slots/depressions of the opposing surface. 3b further illustrates a disc implant with a rugged outer surface (11).

FIG. 4.

Figure 4A:
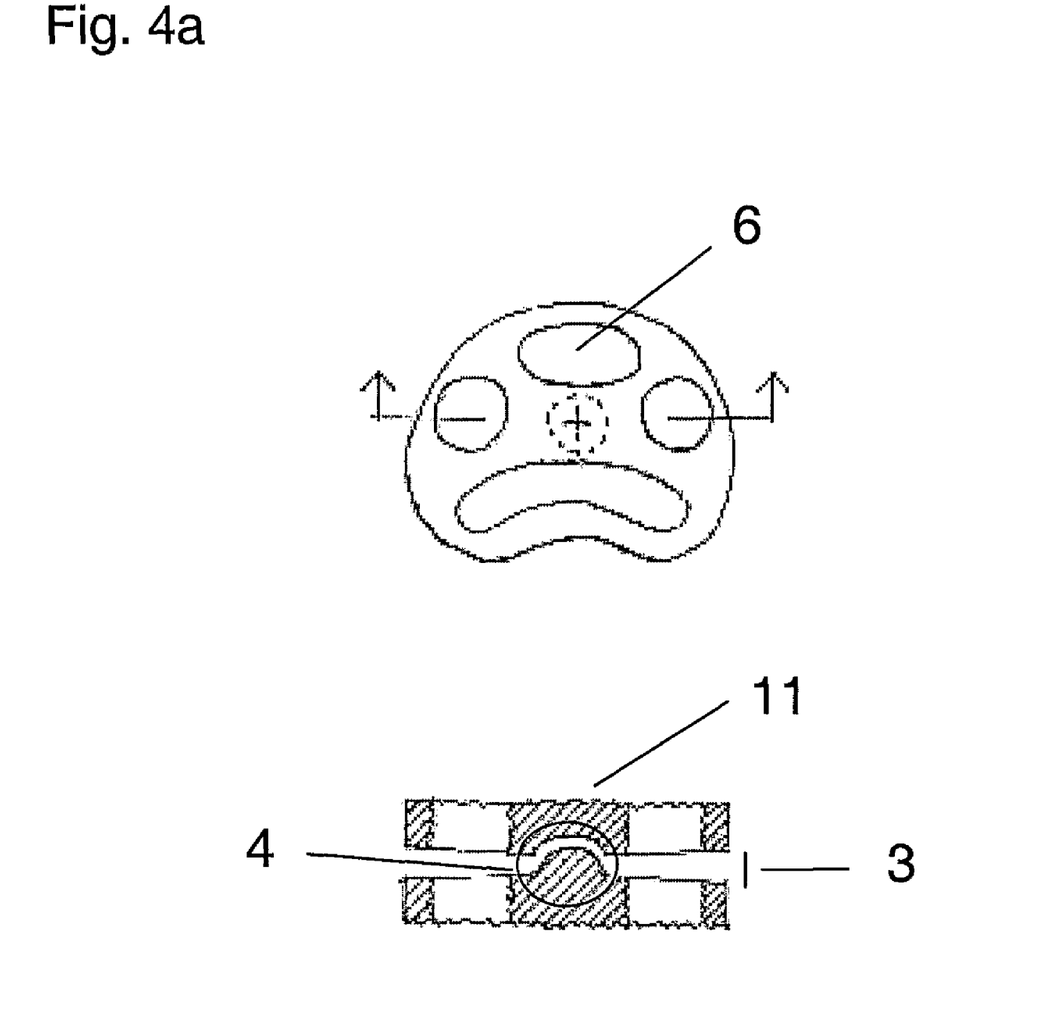
Figure 4B:
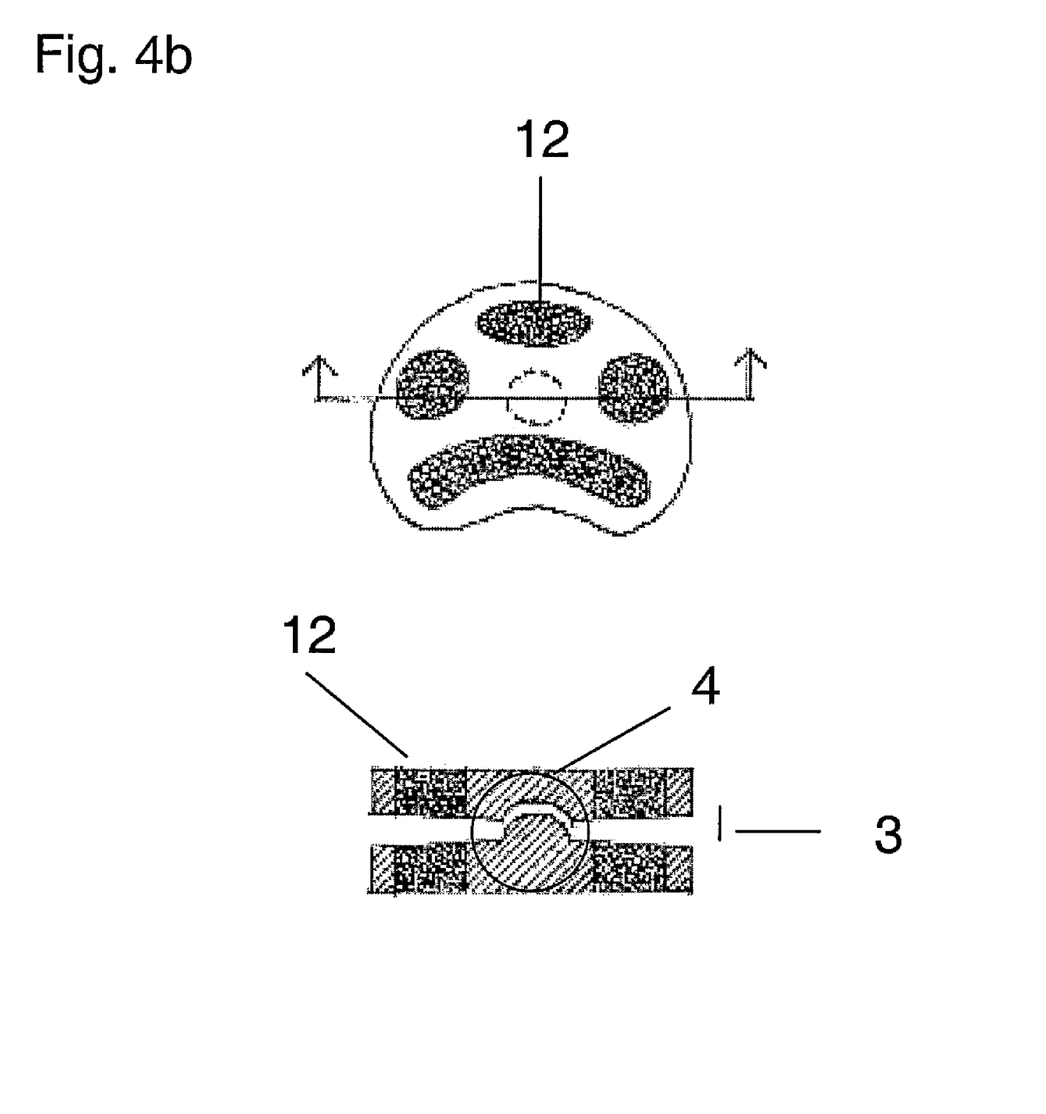

As an alternative to relatively many minor openings, the disc elements may as shown in FIG. 4a comprise few larger openings (6). In a further embodiment the openings are filled (12) with a suitable material, such as artificial bone (FIG. 4b).

FIG. 5.

The shape of the disc elements may be optimised for different surgical procedures as seen in FIG. 5 displaying a disc implant for Transforaminal Lateral Interbody Fusion. The figure is further an example of how the volume occupied by the openings (6) may be optimised, as the elements are merely frames including coupling means (4).

The invention claimed is:

1. A disc implant for total disc replacement comprising:
  a first inter-vertebral element having a first outer fusion surface and a first internal coupling surface,
  a second inter-vertebral element having a second outer fusion surface and a second internal coupling surface,
  a coupling mechanism for movably connecting said first and second elements, the coupling mechanism being positioned in an intermediate space between the first inter-vertebral element and the second inter-vertebral element and allowing movement of the first and second element relative to each other in the absence of bone ingrowth into the intermediate space,
  wherein each of the first intervertebral element and the second inter-vertebral element includes osseointegrative openings or incisions that occupy at least 10% of the surface area of the outer fusion surfaces, thereby facilitating fixation of the first and second inter-vertebral elements relative to each other over time in response to bone ingrowth into the intermediate region through the osseointegrative openings or incisions.

2. The disc implant according to claim 1, where in said coupling mechanism comprises:

a protuberance on the first element and a concave indentation on the second element for receiving said protuberance of said first element, or a ball or plate positioned between the first and the second elements, both elements having indentations for receiving such ball or plate.

3. The disc implant according to claim 1, wherein the first and second inter-vertebral elements each comprise one or more osseointegrative openings.

4. The disc implant according to claim 1, wherein the osseointegrative openings of the first and second inter-vertebral elements oppose each other when the inter-vertebral elements are engaged with each other via the coupling mechanism.

5. The disc implant according to claim 1, wherein the inter-vertebral elements are constructed of metal, or metal alloys, or a combination thereof 6. The disc implant according to claim 1, wherein the osseointezrative openings are filled with a bioceramic material.

7. The disc implant according to claim 6, wherein the bioceramic material is selected from the group consisting of hydroxyapatite, tricalcium phosphate, and mixtures of the two.

8. The disc implant according to claim 1, wherein at least a part of the inter-vertebral elements is coated.

9. The disc implant according to claim 8, wherein the coating is protective.

10. The disc implant according to claim 8, wherein the coating comprises one or more osteoinductive or osteogenic agents.

11. The disc implant according to claim 1, wherein the first and second inter-vertebral elements define openings that define internal surfaces and wherein the internal surfaces of the openings are covered by a coating.

12. The disc implant according to claim 1, wherein the coupling mechanism is provided by a protuberance and an indentation.

13. The disc implant according to claim 12, wherein the protuberance is a long and narrow projection.

14. The disc implant according to claim 12, wherein the protuberance is small and circular.

15. The disc implant according to claim 1, wherein the coupling mechanism is provided by ball and socket arrangement.

16. The disc implant according to claim 1, wherein at least one of the first and second inter-vertebral elements is configured to be supported by a posterior stabilization means.

17. The disc implant according to claim 1, wherein the first and second inter-vertebral elements are configured and dimensioned for anterior insertion.

18. The disc implant according to claim 1, wherein the first and second inter-vertebral elements are configured and dimensioned for posterior insertion.

19. The disc implant according to claim 1, wherein the first and second inter-vertebral elements are configured and dimensioned for transforaminal lumbar interbody fusion.

20. The disc implant according to claim 1, wherein the coupling mechanism is selected from the group consisting of:
  (a) a protuberance on the first inter-vertebral element and a concave indentation on the second inter-vertebral element for receiving said protuberance of said first inter-vertebral element,
  (b) a flange on the first inter-vertebral element and a slot on the second inter-vertebral element for receiving said flange of said first inter-vertebral element, and
  (c) a ball or plate positioned between the first and the second inter-vertebral elements, both inter-vertebral elements having indentations for receiving such ball or plate.

21. The disc implant according to claim 1, wherein the inter-vertebral elements of the disc implant are fabricated from a ceramic material, a polymeric material, a metallic material, or a combination thereof.

22. The disc implant according to claim 1, wherein the osseointegrative openings or incisions are filled with an auto or allograft of bone or a bioceramic material.

* * * * *